(12) United States Patent
Guan et al.

(10) Patent No.: US 9,792,555 B2
(45) Date of Patent: Oct. 17, 2017

(54) PROBABILISTIC MODELING AND SIZING OF EMBEDDED FLAWS IN ULTRASONIC NONDESTRUCTIVE INSPECTIONS FOR FATIGUE DAMAGE PROGNOSTICS AND STRUCTURAL INTEGRITY ASSESSMENT

(71) Applicants: Xuefei Guan, Princeton, NJ (US); Jingdan Zhang, Bellevue, WA (US); Shaohua Kevin Zhou, Plainsboro, NJ (US); Kai Kadau, Clover, SC (US); Yan Guo, Orlando, FL (US); El Mahjoub Rasselkorde, Monroeville, PA (US); Waheed A. Abbasi, Murrysville, PA (US); Chin-Sheng Lee, Winter Springs, FL (US); Ashley L. Lewis, Oviedo, FL (US); Steve H. Radke, Orlando, FL (US)

(72) Inventors: Xuefei Guan, Princeton, NJ (US); Jingdan Zhang, Bellevue, WA (US); Shaohua Kevin Zhou, Plainsboro, NJ (US); Kai Kadau, Clover, SC (US); Yan Guo, Orlando, FL (US); El Mahjoub Rasselkorde, Monroeville, PA (US); Waheed A. Abbasi, Murrysville, PA (US); Chin-Sheng Lee, Winter Springs, FL (US); Ashley L. Lewis, Oviedo, FL (US); Steve H. Radke, Orlando, FL (US)

(73) Assignee: Siemens Energy, Inc., Orlando, FL (US)

( * ) Notice: Subject to any disclaimer, the term of this patent is extended or adjusted under 35 U.S.C. 154(b) by 917 days.

(21) Appl. No.: 14/106,919

(22) Filed: Dec. 16, 2013

(65) Prior Publication Data
US 2014/0229149 A1 Aug. 14, 2014

Related U.S. Application Data

(60) Provisional application No. 61/748,846, filed on Jan. 4, 2013.

(51) Int. Cl.
G06N 7/00 (2006.01)
G06F 17/50 (2006.01)
G01N 29/44 (2006.01)

(52) U.S. Cl.
CPC ......... G06N 7/005 (2013.01); G01N 29/4472 (2013.01); G06F 17/5009 (2013.01);
(Continued)

(58) Field of Classification Search
None
See application file for complete search history.

(56) References Cited

U.S. PATENT DOCUMENTS

2008/0177516 A1* 7/2008 Vasudevan ............ B64F 5/0045
703/2
2012/0209538 A1 8/2012 Yu
(Continued)

OTHER PUBLICATIONS

Karandikar et al., "Prediction of remaining useful life for fatigue-damaged structures using Bayesian inference", Engineering Fracture Mechanics, vol. 96, Dec. 2012, pp. 588-605.*
(Continued)

Primary Examiner — Omar Fernandez Rivas
Assistant Examiner — Herng-Der Day

(57) ABSTRACT

A method for probabilistic fatigue life prediction using nondestructive testing data considering uncertainties from nondestructive examination (NDE) data and fatigue model parameters. The method utilizes uncertainty quantification models for detection, sizing, fatigue model parameters and inputs. A probability of detection model is developed based on a log-linear model coupling an actual flaw size with a
(Continued)

nondestructive examination (NDE) reported size. A distribution of the actual flaw size is derived for both NDE data without flaw indications and NDE data with flaw indications by using probabilistic modeling and Bayes theorem. A turbine rotor example with real world NDE inspection data is presented to demonstrate the overall methodology.

17 Claims, 11 Drawing Sheets

(52) U.S. Cl.
CPC ............... *G01N 2203/0066* (2013.01); *G01N 2203/0073* (2013.01); *G01N 2203/0214* (2013.01); *G01N 2291/0258* (2013.01)

(56) References Cited

U.S. PATENT DOCUMENTS

2013/0268214 A1* 10/2013 Guan ................. G01N 29/4472
702/34
2015/0324697 A1* 11/2015 Nishida ............... G01M 5/0033
706/46

OTHER PUBLICATIONS

Zarate et al., "Bayesian model updating and prognosis of fatigue crack growth", Engineering Structures, vol. 45, Dec. 2012, pp. 53-56.*

PCT International Search Report mailed Mar. 27, 2014 corresponding to PCT International Application No. PCT/US2013/075905 filed Dec. 18, 2013 (12 pages).

Xuefei, Guan et al.: "Model selection updating, and averaging for probabilistic fatigue damage prognosis"; in Structural Safety; vol. 33; No. 3; pp. 243,248; DOI 10.1016/J.STRUSAFE.2011.03.006; XP02808809; NL; Mar. 16, 2011.

Shankar, Sankararaman et al.: "Uncertainty quantification and model validation of fatigue crack growth prediction" in: Engineering Fracture Mechanis, Pergamon Press; vol. 78; No. 7; pp. 1487-1504; DOI 10.1016/J.ENGFRACHMECH.2011.02.017; XP028194449; 2011; Feb. 21, 2011.

Berens, A. P.: "NDE Reliability Data Analysis"; in ASM Handbook; vol. 17, pp. 689-701; DOI 10.1361/ASMHBA0002238; XP009176989; Jan. 1, 1989.

* cited by examiner

PROBABILISTIC MODELING AND SIZING OF EMBEDDED FLAWS IN ULTRASONIC NONDESTRUCTIVE INSPECTIONS FOR FATIGUE DAMAGE PROGNOSTICS AND STRUCTURAL INTEGRITY ASSESSMENT

CROSS REFERENCE TO RELATED APPLICATION

This application claims the benefit under 35 U.S.C. §119(e) of U.S. Provisional Application No. 61/748,846 entitled PROBABILISTIC MODELING AND QUANTIFICATION OF EMBEDDED FLAWS IN ULTRASONIC NON-DESTRUCTIVE INSPECTION AND ITS APPLICATION filed on Jan. 4, 2013 which is incorporated herein by reference in its entirety and to which this application claims the benefit of priority.

FIELD OF THE INVENTION

This patent application relates to methods for probabilistic fatigue life prediction considering uncertainties from nondestructive examination (NDE) data and fatigue model parameters.

BACKGROUND OF THE INVENTION

Steel and alloy structures are essential parts of civil, aviation, marine, and power generation systems. Nondestructive examination (hereinafter "NDE") and nondestructive (hereinafter "NDT") techniques have been an effective measure to evaluate the manufacturing quality and operational integrity of those structures and systems since the early 1970's. Many NDT and NDE techniques include ultrasonic inspection, magnetic particle inspection, electromagnetic inspection, radiographic inspection, penetrant inspection, acoustic emission and visual inspection. In particular, state-of-the-art ultrasonic NDE techniques provide an opportunity to obtain the information about internal flaws of a structure, such as voids and cracks, without damaging the structure. This information can be integrated with fracture mechanics and material properties, allowing for fatigue life prediction and risk management.

Scheduled NDEs are sometimes mandatory for structures experiencing time-dependent degradations. Inservice or field inspections are more difficult than inspections in manufacturing phases, and uncertainties in flaw identification and sizing can be much larger due to the more complex conditions for testing. The quality of NDE depends on many uncertain factors, including the sensitivity of inspection instrument, the service condition of the target structure being inspected, the variability of material properties, operation procedure and personnel and others. It would be desirable to have scientific quantification of these uncertainties in order to produce reliable and informative inspection results. Typically, deterministic treatment of the uncertainty includes the use of safety factors. However, the determination of safety factors substantially relies on experience and expert judgment, which is not a trivial task for inspection personnel such as engineers who do not have strong field knowledge.

SUMMARY OF THE INVENTION

A method for probabilistic fatigue life prediction considering uncertainties from nondestructive examination (NDE) data and fatigue model parameters is disclosed. The method includes providing a probability of detection model and an initial crack size probability density function (PDF). The method also includes providing probabilistic identification of model parameters and providing a model parameter PDF. Next, the method includes providing a crack growth model based on the initial crack size, the model parameter PDF and material/load factors. Further, the method includes determining uncertainty propagation and providing fatigue life prediction based on the uncertainty propagation and crack growth model.

In particular, the method utilizes uncertainty quantification models for detection, sizing, fatigue model parameters and inputs. A probability of detection model is developed based on a log-linear model coupling an actual flaw size with a nondestructive examination (NDE) reported size. A distribution of the actual flaw size is derived for both NDE data without flaw indications and NDE data with flaw indications by using probabilistic modeling and Bayes theorem.

BRIEF DESCRIPTION OF THE DRAWINGS

FIGS. 10A-10B depict median and 95% CI estimation of PoF wherein FIG. 10A depicts the case where no indication is found in ultrasonic NDE data with a threshold of 1.0 mm and FIG. 10B depicts the case with a 1.8 mm indication.

DESCRIPTION OF THE INVENTION

Figure 1:
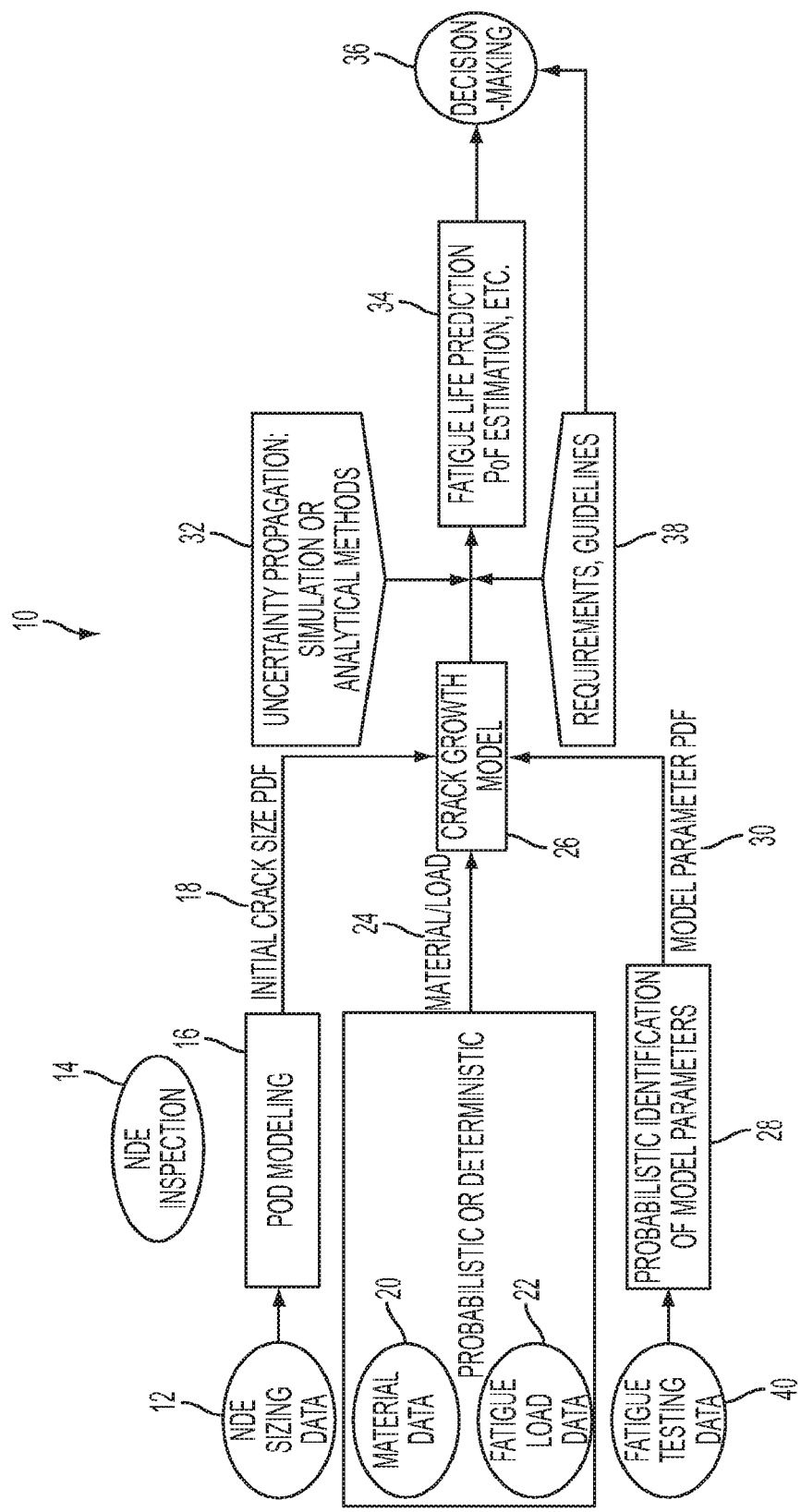
FIG. 1 depicts a method of probabilistic fatigue life prediction with nondestructive examination (NDE) inspection data in accordance with the invention.

Exemplary embodiments of the invention as described herein generally include systematic method for probabilistic fatigue life prediction considering uncertainties from nondestructive examination (hereinafter "NDE") inspection and fatigue life parameters. While the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention. In addition, the disclosure of U.S. Patent Publication No. 2013/0268214, application Ser. No. 13/855,130, entitled PROBABILISTIC FATIGUE LIFE PREDICTION USING ULTRASONIC INSPECTION DATA CONSIDERING EIFS UNCERTAINTY is herein incorporated by reference it its entirety.

1.0 Outline

Probabilistic methods provide a rational approach for uncertainty management and quantification. The following description is organized as follows. At the outset, probability of detection (hereinafter "POD") modeling is presented using a classical log-linear sizing model to couple ultrasonic NDE reported flaw size and actual flaw size. Next, a probabilistic model for actual flaw size is developed. Following that, an overall procedure of probabilistic fatigue life prediction is described. A real world steam turbine rotor application with ultrasonic NDE data is presented to demonstrate the evaluation for flaw size, fatigue life, and a probability of failure (hereinafter "PoF"). In addition, detection threshold of the ultrasonic NDE system and its influence to the assessment result is described. Interpretation and error analysis of the assessment result is also provided.

2. Probability of Detection Modeling

Two approaches are generally available for POD modeling. One approach uses hit/miss data, which only record whether a flaw was detected or not. This type of data is used for some NDE methods such as penetrant testing or magnetic particle testing. In other NDE inspection systems, additional information is available in testing data. For example, a signal amplitude and time index of ultrasonic NDE signals, and the voltage amplitude and location information in electromagnetic responses. In those cases the flaw size or defect severity is closely correlated with signal responses, and thus the NDE data are referred to as signal response data. Signal response data are usually continuous and denoted as $\hat{a}$. The variable of query is usually denoted as $a$. For example, $a$ can be the actual size of a flaw and $\hat{a}$ is the reported size based on the ultrasonic NDE signal. This current invention considers the signal response data. It has been disclosed in many studies that ln $\hat{a}$ and ln $a$ are usually linearly correlated. See Berens, A. P., "NDE Reliability Data Analysis", ASM Handbook, vol. 17, 1989, pgs. 689-701 (hereinafter "Berens") and Schneider, C., Rudlin, J., "Review of Statistical Methods Used in Quantifying NDT Reliability", Insight-Non-Destructive Testing and Condition Monitoring, 1 Feb. 2004, vol. 46, no. 2, pgs. 77-79, both of which are hereby incorporated by reference in their entirety. The correlation can be expressed as $$\ln \hat{a} = \alpha + \beta \ln a + \epsilon, \quad (1)$$

where $\epsilon$ is a normal random variable with zero mean and standard deviation $\sigma_\epsilon$. Both $\alpha$ and $\beta$ are fitting parameters. A pre-defined threshold $\hat{a}_{th}$ is assumed according to the measurement noise and physical limits of measuring devices. It is also possible that $\hat{a}_{th}$ is specified by manufacturing criterion and standard. For example, a vendor may consider indications less than 1.0 mm are safe to be ignored. A flaw is regarded as identified if $\hat{a}$ exceeds the threshold value of $\hat{a}_{th}$, and the probability of detection of size a can be expressed as $$POD(a) = Pr(\ln \hat{a} > \ln \hat{a}_{th}), \quad (2)$$

where $Pr(\cdot)$ represents the probability of an event $(\cdot)$. Using Eq. (1), the POD function is rewritten as $$POD(a) = Pr(\alpha + \beta \ln a + \epsilon > \ln \hat{a}_{th}) = \Phi\left(\frac{\ln a - (\ln \hat{a}_{th} - \alpha)/\beta}{\sigma_\epsilon/\beta}\right), \quad (3)$$

where $\Phi(\cdot)$ is the standard normal cumulative distribution function (hereinafter "CDF"). If the variable $\epsilon$ follows another probability distribution other than the standard normal distribution, the corresponding CDF of $\epsilon$ should be used.

The log-linear model is one of the most widely-used models due to its relatively simple model structure and the property that the flaw size $a$ is ensured to be a positive scalar. Other models, such as a linear model or other physics-based model can also be used to couple the reported flaw size and the actual flaw size. Choosing a particular model format from all available model formats depends on factors such as applications, data characteristics, and inspection systems. From the perspective of model performance, considering model complexity, generality and its predictive power, Bayesian method provides a probabilistic measure for choosing a model based on the concept of Bayes factor. See Kass, R., Raftery, A., "Bayes Factors", Journal of the American Statistical Association, 1995, volume 90, no. 430, pgs. 773-795 and Guan, X., Jha, R., Liu, Y., "Model Selection, Updating, and Averaging for Probabilistic Fatigue Damage Prognosis", Structural Safety, May 2011, vol. 33, issue 3, pgs. 242-249 both which are hereby incorporated by reference in their entirety. Alternatively, any distribution can be used and evaluated by applying the assumption made in Eq. (2) and utilizing Monte Carlo methods to numerically determine the POD. Further, it has been determined that raw data revealing the correlation between the NDE signal and the true flaw size can also be used to numerically determine the POD. See Kern, T., Ewald, J., Maile, K., "Evaluation of NDT-Signals for Use in the Fracture Mechanics Safety Analysis", Materials at High Temperatures, 1998; 15(2): 107-110 (hereinafter "Kern").

3. Probabilistic Flaw Size Modeling Under POD

Following convention, random variables are denoted using capital letters (e.g., $\hat{A}$) and corresponding values are denoted using lower case letters (e.g., $\hat{a}$). Assume that a flaw is detected using NDE and the value of the reported flaw size is a', where a' is a positive real scalar. For convenience, the variable in $\hat{A}$ is used instead of $\hat{A}$. Represent probability distributions for propositions ln $\hat{A} \in (\ln \hat{a}, \ln \hat{a} + d \ln \hat{a})$, ln $A \in (\ln a, \ln a + d \ln a)$, and $E \in (\epsilon, \epsilon + d\epsilon)$ by functions $p(\ln \hat{A}) = f_{\ln \hat{A}}(\ln \hat{a})$, $p(\ln A) = f_{\ln A}(\ln a)$, and $p(E) = f_E(\epsilon)$, respectively. The probability distribution of the actual flaw size, $p(\ln A)$, is of interest and its derivation is presented below.

Denote D as the event of a flaw is identified and $\overline{D}$ is the event that a flaw is not identified. The joint probability distribution $p(\ln A, \ln \hat{A}, E|D)$ can be used to obtain $p(\ln A|D)$ as $$p(\ln A|D) = \iint p(\ln A, \ln \hat{A}, E|D) d \ln \hat{A} dE. \quad (4)$$

The physical meaning of event D represents the fact that an indication of flaw was identified from the NDE inspection data and the resulting reported flaw size is a'. It can be further expressed, under the condition that ln Â and E are independent, as $$p(\ln A|D) = \iint p(\ln A|\ln \hat{A}, E, D) p(\ln \hat{A}|D) p(E|D) d \ln \hat{A} dE. \quad (5)$$

Since ln â = α + β ln a + ε, $$p(\ln A|\ln \hat{A}, E, D) = \delta(\ln \hat{a} - \alpha - \beta \ln a - \epsilon), \quad (6)$$

where $\delta(\cdot)$ is the Dirac delta function. Substitute Eq. (6) into Eq. (5) to obtain $$p(\ln A|D) = \int_R f_{\ln \hat{A}}(\ln \hat{a}) f_E(\ln \hat{a} - \alpha - \beta \ln a) d \ln \hat{a}. \quad (7)$$

The result of Eq. (7) is now applied as follows.

3.1 Deterministic Conversion Model

Denote a raw signal feature, such as the maximum echo amplitude in the ultrasonic NDE, as x, and the conversion is made through a mathematical model m(x). It is clear that if the model is perfect m(x)=ln â which leads to $$f_{\ln \hat{A}}(\ln \hat{a}) = \delta(\ln \hat{a} - m(x)). \quad (8)$$

Substitution of Eq. (8) into Eq. (7) yields (recalling the actual value of m(x) is now ln a')

$$p(\ln A|D) = \int_R \delta(\ln \hat{a} - m(x)) f_E(\ln \hat{a} - \alpha - \beta \ln a) d \ln \hat{a} = f_E(\ln a' - \alpha - \beta \ln a). \quad (9)$$

Recall $f_E(\cdot)$ is a normal probability density function (hereinafter "PDF") with zero mean and standard deviation $\sigma_\epsilon$. It is symmetric and $\alpha + \beta \ln a - \ln a'$ also follows a normal distribution with zero mean and standard deviation $\sigma_\epsilon$. Recognize that ln A follows a normal PDF with mean (ln a' − α)/β and standard deviation $\sigma_\epsilon/\beta$, and thus A is a log-normal variable. The PDF of variable A is $$p(A|D) = f_{A|D}(a) = \frac{1}{a(\sigma_\epsilon/\beta)} \phi\left(\frac{\ln a - (\ln a' - \alpha)/\beta}{\sigma_\epsilon/\beta}\right), \quad (10)$$

where $\phi(\cdot)$ is the standard normal PDF.

3.2 Probabilistic Conversion Model

If the conversion model is uncertain and the difference between the model output m(x) and the estimated size ln a is a random quantity e, $$\ln \hat{a} = m(x) + e. \quad (11)$$

Denote the random variable as E, and the probability distribution function for E as $f_E(e)$. It is quite common to make the assumption that E is a normal variable with zero mean and standard deviation of $\sigma_e$.

$$p(\ln \hat{A}|D) = \int p(\ln \hat{A}, E|D) p(E|D) dE. \quad (12)$$

Since ln â = m(x) + e, $$p(\ln \hat{A}, E|D) = \delta(\ln \hat{a} - m(x) - e). \quad (13)$$

and $$p(\ln \hat{A}|D) = f_{\ln \hat{A}}(\ln \hat{a}) = \int_R \delta(\ln \hat{a} - m(x) - e) f_E(e) de = f_E(\ln \hat{a} - m(x)). \quad (14)$$

Substitute Eq. (14) into Eq. (7), with the actual value of m(x)=ln a', to obtain $$p(\ln A|D) = \int_R f_E(\ln \hat{a} - \ln a') f_E(\ln \hat{a} - \alpha - \beta \ln a) d \ln \hat{a}. \quad (15)$$

Recognizing Eq. (15) is a convolution of two normal probability distributions, it is well known that the result is another normal distribution with a mean value of (ln a' − α)/β and a standard deviation of $\sqrt{\sigma_e^2 + \sigma_\epsilon^2}/\beta$. Again, ln A is a normal variable and A is a log-normal variable with the following PDF, $$p(A|D) = f_{A|D}(a) = \frac{1}{a\left(\sqrt{\sigma_e^2 + \sigma_\epsilon^2}/\beta\right)} \phi\left(\frac{\ln a - (\ln a' - \alpha)/\beta}{\sqrt{\sigma_e^2 + \sigma_\epsilon^2}/\beta}\right). \quad (16)$$

It can be seen that if the degree of the uncertainty associated with the conversion model is approaching zero, i.e., $\sigma_e \to 0$, Eq. (16) reduces to Eq. (10). In addition, if the uncertainty in variable E is approaching zero, i.e., $\sigma_\epsilon > 0$, ln a = (ln a' − α)/β.

3.3 No Indication Found in NDE Data

A clean NDE inspection data does not indicate the target structure is completely free of flaws due to the inherent uncertainty and the inspection threshold $\hat{a}_{th}$. The distribution of A can readily be expressed using Bayes' theorem as $$p(A|\overline{D}) = \frac{p(A, \overline{D})}{p(\overline{D})} = \frac{p(\overline{D}|A) p(A)}{p(\overline{D})}, \quad (17)$$

where p(A) is the prior probability distribution of the flaw size, and $p(\overline{D}|A)$ is the probability of the event that no indication is found when a flaw actually exists. It should be noted that this usually requires some sort of NDE data base of prior inspections in order to have information about the flaw distribution of the fleet. Denote the prior PDF of A as $f_A(a)$. Using the concept of POD and Eq. (3), the probability of the event that the size of a flaw is not larger than a given value a conditional on clean NDE data is $$Pr(A \le a|\overline{D}) = \frac{\int_0^a [1 - POD(a)] f_A(a) da}{\int_0^\infty [1 - POD(a)] f_A(a) da}. \quad (18)$$

The probability distribution of a flaw with size a conditional on clean NDE data is $$p(A|\overline{D}) = f_{A|\overline{D}}(a) = \frac{\partial [Pr(A \le a|\overline{D})]}{\partial a} = \frac{[1 - POD(a)] f_A(a)}{\int_0^\infty [1 - POD(a)] f_A(a) da}, \quad (19)$$

where POD(a) is given in Eq. (3) and $f_A(a)$ is the prior PDF of the actual flaw size. It is noted that the above method is for ultrasonic NDE applications. However, the current invention can directly used for modeling other types of inspections, such as eddy-current inspections, magnetic particles inspections and others.

4. Probabilistic Fatigue Life Prediction with NDE Inspection Data

Fatigue life prediction relies on analytical models of fatigue crack propagation mechanisms. An important element in the fatigue crack growth model is the initial crack size. The initial flaw size estimation based on NDE data has been previously described. Since there are errors and uncertainties inherent in the inspection process, a maintenance plan should be made based on analytical predictions, inspection data and uncertainties in the inspection techniques as well as life-cycle cost.

Uncertainties due to material properties, geometries, loading, as well as NDE inspection must be carefully included and quantified in fatigue life prediction. In general, uncertainties from material properties and geometries affect the final result through fatigue model parameters. Fatigue model parameters, for example, C and m in a known Paris' equation (see Eq. (21) as will be described hereinafter) are typically estimated from fatigue crack growth testing data. Methods such as maximum likelihood estimate (hereinafter "MLE") method, least square fitting and Bayesian parameter estimation are commonly used. The fatigue crack growth testing is usually conducted for multiple specimens. Therefore, uncertainties from material properties and specimen geometries are statistically encoded in the probabilistic distribution of the model parameters regressed on the experimental data. The uncertainty modeling for fatigue loads depends on different applications. For example, the fatigue load of a generator rotor is a combination of thermal stress, residual stress (from manufacturing), and the centrifugal stress introduced by rotation. The operation plan does not change significantly and the fatigue load cycles formed by a start-up and shutdown has a relatively small variation. However, the fatigue load of a bridge, for example, might be very complex due to stochastic traffic flows. In case no indication is found in NDE inspection data, there is still a possibility that some flaws exist in the structure. This is due to the inherent uncertainty of NDE inspection and the detection threshold $\hat{a}_{th}$. Uncertainties propagate through the fatigue crack growth model, e.g., Paris' equation. Simulation based methods such as Monte Carlo (hereinafter "MC") simulations can be used to obtain probabilistic life prediction results. The process is straightforward. At the outset, a large set of random instances for model parameters, initial flaw size, and all other involved uncertain variables are generated. The fatigue life using each of the random instances is then calculated. With a large number of random instances, the distribution of the fatigue life instances is ensured to converge to its theoretical distribution. Analytical methods are also available to obtain the probabilistic life prediction results without using simulations. See Guan, X., He, J., Jha, R., Liu, Y., "An Efficient Analytical Bayesian Method for ReliaBility and System Response Updating Based on Laplace and Inverse First-Order Reliability Computations", Reliability Engineering & System Safety, 2012, vol. 97, issue 1, pgs. 1-13 the disclosure of which is hereby incorporated by reference.

The PDF of fatigue model parameters is obtained using the fatigue crack growth testing data, i.e., crack growth rate vs. stress intensity factor range (da/dN vs. ΔK). Based on the crack growth model, linear or nonlinear regression on crack growth testing data can be used to obtain the PDF of model parameters. See Guan, X., Giffin, A., Jha, R., Liu, Y., "Maximum Relative Entropy-Based Probabilistic Inference in Fatigue Crack Damage Prognostics", Probabilistic Engineering Mechanics, July 2012, vol. 29, pgs. 157-166.

A method 10 of probabilistic fatigue life prediction with NDE inspection data in accordance with the invention is shown in FIG. 1. The method 10 will be described in conjunction with a real world example set forth in section 5 of the current patent application entitled "Application example." The method 10 includes utilizing NDE sizing data 12 and NDE inspection data 14 to develop a POD model at step 16 as set forth in Eq. (3) wherein parameters α, β and ε are estimated using Eq. (1). At step 18, an initial crack size PDF is then obtained using either a deterministic conversion model per Eq. (10) or a probabilistic conversion model per Eq. (16) if flaw indications are found. If no flaw indications are found, then Eq. (19) is used.

The method 10 also includes utilizing Material data 20 and Fatigue load data 22 to obtain material/load factors at step 24. In particular, load refers to the stress term σ in Eq. 22 as will be described. The current invention takes into consideration uncertainty due to material factors. For example, in one embodiment, the method 10 includes the use of a known Paris equation (Eq. 21) as will be described to provide a fatigue crack growth model 26. If a different fatigue crack growth model is used, a material property such as Young's modulus may be a term of the model. If Young's modulus is described using a probability distribution, its uncertainty can then be included in the calculation.

The method 10 further includes a probabilistic identification of model parameters at step 28 based on fatigue testing data 40. In this step, a Bayesian parameter estimation method is used to estimate model parameters (in C, m) of the Paris equation (Eq. 21). A model parameter PDF is then generated at step 30 in accordance with Eq. 23. The initial crack size PDF from step 28, material/load factors from step 24 and model parameter PDF from 30 are then used to determine a crack growth model at step 26. In accordance with the invention, the crack growth model is given by the Paris' equation (Eq. 21). Since crack growth models are semi-empirical, it is noted that other crack growth models can be used instead of the Paris' equation.

In addition, the method 10 includes an uncertainty propagation step 32 which refers to using an analytical method or a simulation-based method to calculate fatigue life and PoF using fatigue crack growth model of Eq. 21 set forth in section 5.4 as will be described. At step 34, a fatigue life prediction is obtained by calculating fatigue life given a fatigue crack growth model (Eq. 21), initial crack size obtained in step 18 and a critical crack size (Eq. 24) as will be described in section 5.4. Decision making regarding a maintenance plan is then performed at step 36. In this step, a maintenance plan is determined by a turbine manufacturer based on requirement/guidelines 38, inspection results and life prediction analysis. The maintenance plan is then provided to a power plant operator. The power plant operator then decides a course of action (such as repair, replace a damaged part) based on the results provided by the manufacturer.

5. Application Example

A steam turbine rotor is of interest for fatigue life prediction and structural integrity assessment. The rotor, which is a solid rotor, is made of Chromium-Molybdenum-Vanadium (hereinafter "Cr—Mo—V") material and is subject to fatigue loads. Ultrasonic NDE inspections are performed to identify internal flaws for fatigue life evaluations. Creep crack growth is not considered in this example due to the operational temperature of 800 degrees F.

5.1 Uncertainty Quantification of Ultrasonic NDE and POD

For illustration purposes, historical ultrasonic NDE sizing information disclosed in Schwant, R., Timo, D., "Life Assessment of General Electric Large Steam Turbine Rotors", in Life Assessment and Improvement of Turbo-Generator Rotors for Fossil Plants, Pergamon Press, New York, 1985, pgs. 1-8, hereinafter "Schwant", the contents of which are herein incorporated by reference in their entirety, are used to represent the actual detection features of the ultrasonic inspection. It is understood that other sizing information may be used.

Figure 2A:
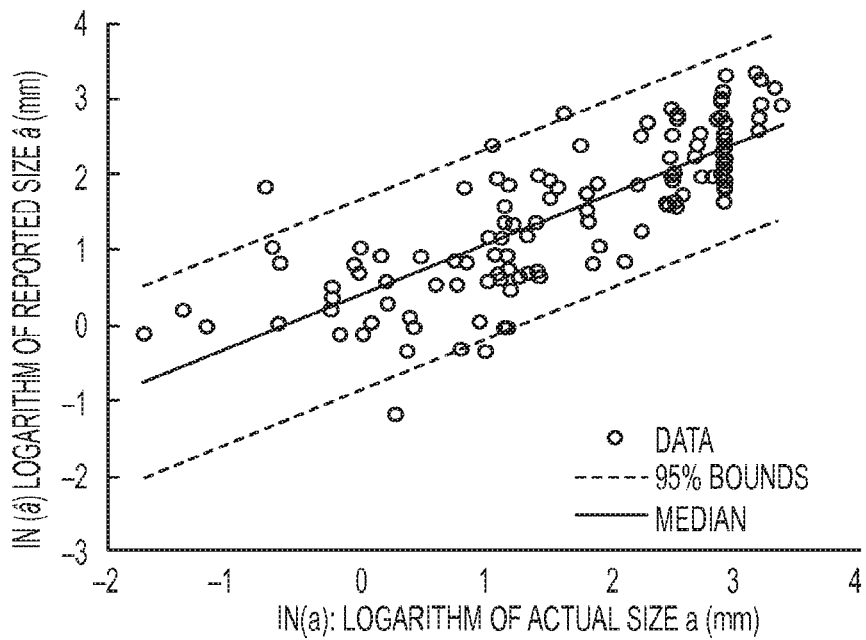
FIG. 2A depicts sizing information of actual flaw size and ultrasonic NDE inspection reported size.

Referring to FIG. 2A, sizing information of actual flaw size and ultrasonic NDE inspection reported size as disclosed in Schwant are shown in logarithmic scale. The x-axis is the actual flaw size (e.g., diameter of the flaw reflector) measured after cutting the rotor apart to expose the internal flaw. The y-axis is the ultrasonic inspection reported flaw size (e.g., diameter of an equivalent reflector) before cutting the rotor apart. Due to the uncertainty in ultrasonic inspection, the reported flaw size for an individual physical flaw is different from the actual flaw size. Using the log-scale data shown in FIG. 2A and linear regression, the coefficient and intercept in Eq. (1) are estimated as $\beta=0.658$, $\alpha=0.381$, respectively. The standard deviation of $\epsilon$ is estimated as $\sigma_\epsilon=0.616$. The mean and 95% bound prediction results are shown in FIG. 2A as solid and dash lines, respectively. For investigation purposes, three values of 0.5 mm, 1.0 mm, and 1.5 mm are considered as the threshold value $\hat{a}_{th}$. The three values are also approximately equal to the 99%, 90%, 85% lower bounds (i.e., 0.01, 0.1, 0.15 quantile values) of all reported size values, respectively. Alternatively, the threshold value can also be estimated based on established techniques (see previously cited Berens). The POD model is expressed as the following equation:

$$POD(a) = \begin{cases} \Phi\left(\dfrac{\ln a + 1.6334}{0.9368}\right) & \hat{a}_{th} = 0.5 \text{ mm} \\ \Phi\left(\dfrac{\ln a + 0.5793}{0.9368}\right) & \hat{a}_{th} = 1.0 \text{ mm} \\ \Phi\left(\dfrac{\ln a - 0.0374}{0.9368}\right) & \hat{a}_{th} = 1.5 \text{ mm} \end{cases} \quad (20)$$

Figure 2B:
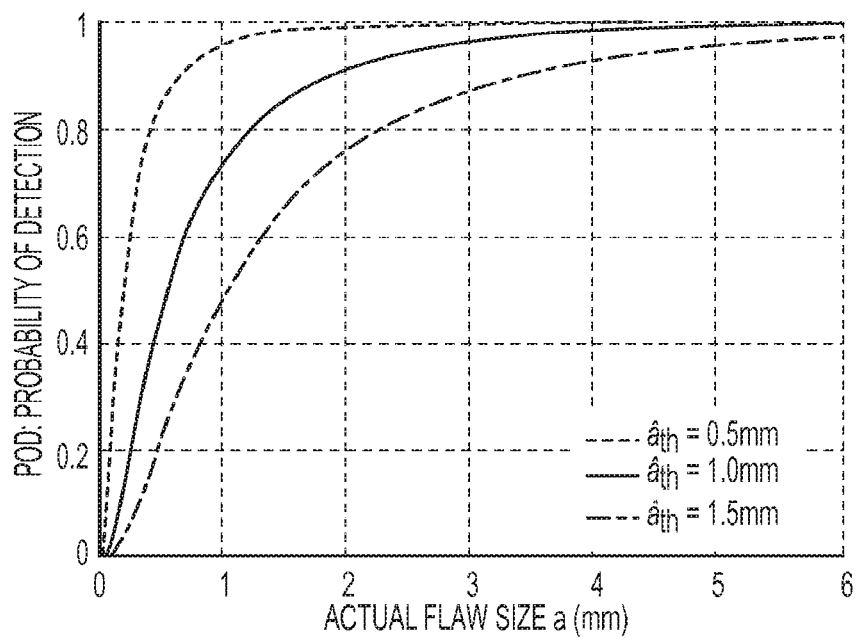
FIG. 2B depicts probability of detection (POD) curves obtained by using sizing data with threshold values of 0.5 mm, 1.0 mm and 1.5 mm.

FIG. 2B depicts POD curves obtained by using sizing data with threshold values of 0.5 mm, 1.0 mm and 1.5 mm. As can be seen from FIG. 2B, the selection of different threshold values $\hat{a}_{th}$ results in different POD curves. Thus, threshold value $\hat{a}_{th}$ is an important factor and should be carefully selected or calculated.

5.2 Initial Crack Size Assumption Based on Ultrasonic NDE Reported Size

When using a method known as distance-gain-size (hereinafter "DGS") as a conversion model to transfer the raw data to a flaw size, the ultrasonic NDE reported size is interpreted as an equivalent reflector (flat bottom holes or side drill holes) size, i.e., the diameter of the hole. The DGS method implies the reflector is smooth, planar and perpendicular to the ultrasound beam axis, and is fully contained within the ultrasound beam. The actual shape and orientation cannot be inferred using the DGS method since the method is substantially based on echo amplitude. Other sizing methods, such as synthetic aperture focusing technique (SAFT), may be used to identify the orientation and extents of a small flaw. Fatigue crack propagation calculation takes the crack size of a chosen crack geometry. For embedded flaws identified by ultrasonic NDE data and sized using the DGS method, the flaw is assumed to be an embedded elliptical crack.

Figure 3A:
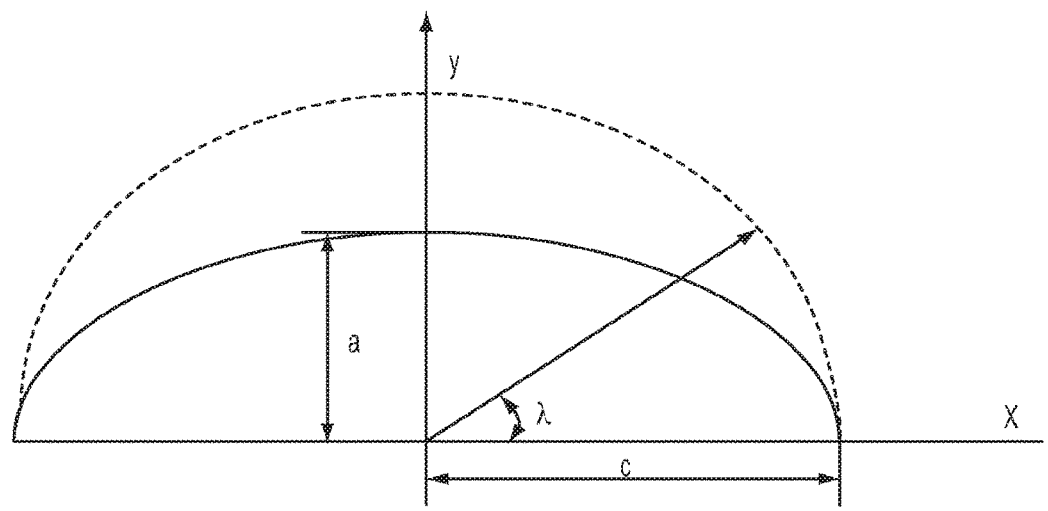
FIG. 3A depicts a diagram for embedded elliptical crack geometry.
Figure 3B:
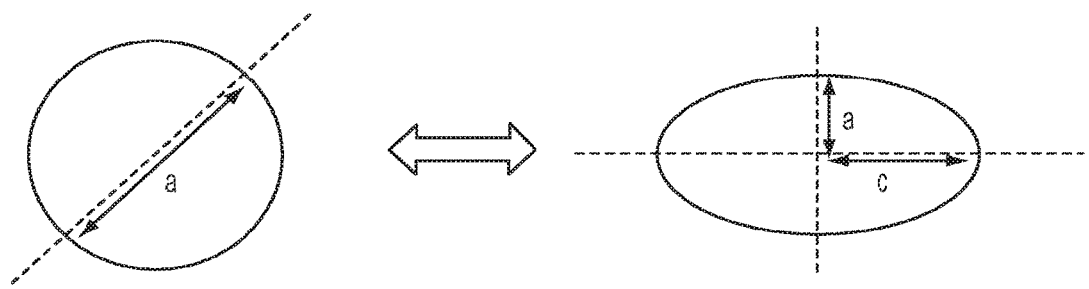
FIG. 3B depicts an accepted assumption that an elliptical area of an embedded elliptical flaw is equal to a reported reflector area.

FIG. 3A depicts a diagram of the embedded elliptical crack geometry, where a is the initial crack size (i.e. minor axial length). Since the actual flaw shape and orientation is unknown, an assumption is made to transfer the NDE reported size (diameter of the reflector) to the length of an embedded elliptical crack. Referring to FIG. 3B, "a" is the diameter of the ultrasonic reported equivalent reflector size. An accepted assumption is based on the idea that the elliptical area of an embedded elliptical flaw is equal to the reported reflector area (see previously cited Kern). For instance, given a flaw with an equivalent reflector size of 3 mm and a/c=0.2, the equivalent crack size for fatigue analysis is calculated according to $\pi(3 \text{ mm})^2/4=\pi ac$ and is approximately 0.67 mm.

5.3 Uncertainty Quantification for Fatigue Model Parameters

Figure 4A:
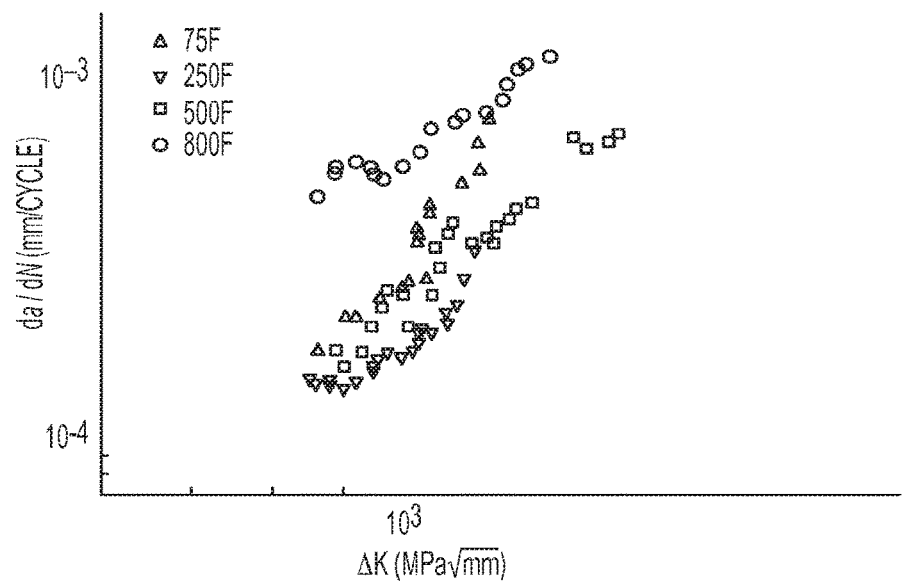
FIG. 4A depicts fatigue testing data from for Chromium-Molybdenum-Vanadium material at different temperatures.

The model parameter uncertainty is quantified using fatigue testing data of Cr—Mo—V material. The fatigue testing data of Cr—Mo—V material disclosed in Shih, T., Clarke, G., "Effects of Temperature and Frequency on the Fatigue Crack Growth Rate Properties of a 1950 Vintage CrMoV Rotor Material", Fracture Mechanics: Proceedings of the Eleventh National Symposium on Fracture Mechanics, vol. 700, ASTM International, 1979, p. 125, hereinafter "Shih", the contents of which are herein incorporated by reference in their entirety, are used in the following description. Referring to FIG. 4A, the fatigue testing data from Shih for Cr—Mo—V material at different temperatures is shown. Crack growth data at 800 degrees F. under constant loading are used to perform Bayesian parameter estimation using the Paris' equation for embedded elliptical crack geometry. Paris' equation is given in the following equation:

$$da/dN = C(\Delta K)^m, \quad (21)$$

where a is the crack size, N is the number of load cycles, C and m are model parameters need to be identified from fatigue testing data, and $\Delta K$ is the stress intensity factor range during one load cycle. For an embedded elliptical crack as shown in FIG. 3A, the stress intensity factor of a point located at an angle $\lambda$ with respect to the direction of the applied tensile stress $\sigma$ is given by $$K = \sigma\sqrt{\pi a M}/Q[\sin^2 \lambda + (a/c)^2 \cos^2 \lambda]^{1/4}, \quad (22)$$

where M is a location factor, a the crack size previously defined which is also the minor axis length of the semi-ellipse and c is the major axis length of the semi-ellipse. Term Q is the shape factor defined as $$Q = \int_0^{\pi/2} \sqrt{1 - \left(\dfrac{c^2 - a^2}{c^2}\right)\sin^2\lambda}\, d\lambda.$$

For embedded crack geometry M=1.0. It is noted that the most critical ratio value depends on several factors and can not be easily predicted. For conservative purposes in engineering applications, a/c takes 0.4 and K has a maximum value at $\lambda=\pi/2$. Aspects of Bayesian parameter estimation with Markov chain Monte Carlo (hereinafter "MCMC") methods can be found in Guan, X., Zhang, J., Kadau, K., Zhou, S. K., "Probabilistic Fatigue Life Prediction Using Ultrasonic Inspection Data Considering Equivalent Initial Flaw Size Uncertainty", Thompson, D. O., Chimenti, D. E., editors, AIP Conference Proceedings, vol. 1511, AIP, 2013, pgs. 620-627, the contects of which are hereby incorporated by reference. The joint distribution of (ln C, m) is estimated using 200,000 MCMC samples, considering the two parameters follow a multivariate normal distribution (hereinafter "MVN"):

$$(23) \quad f(\ln C, m) \sim MVN(\mu_{(\ln C, m)}, \Sigma_{(\ln C, m)}).$$

The mean vector is $\mu_{(\ln C, m)} = [-22.23, 2.151]$ and the covariance matrix is $$\sum_{(\ln C, m)} = \begin{bmatrix} 1.2143 & -0.17465 \\ -0.17465 & 0.02513 \end{bmatrix}.$$

Figure 4B:
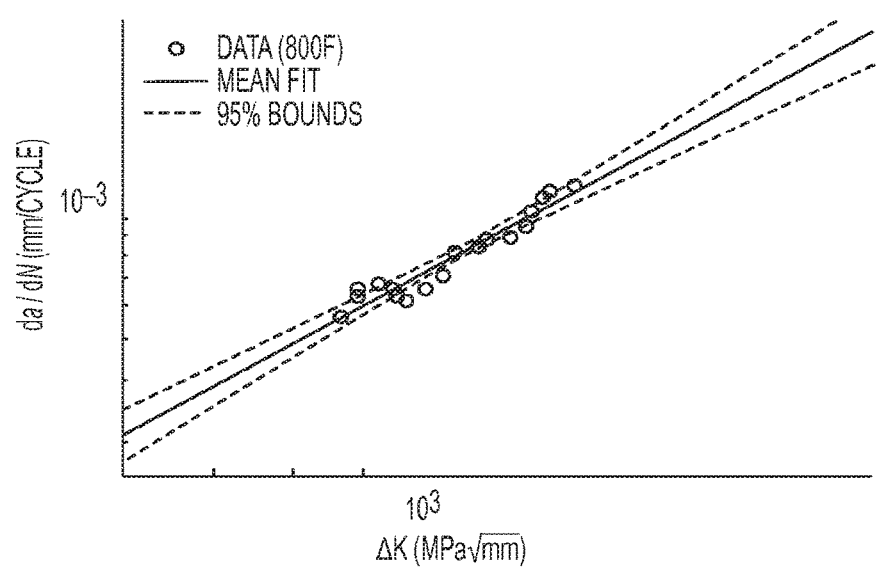
FIG. 4B depicts fitting performance of an estimation wherein mean and 95% bound predictions are shown.

The fitting performance of the estimation is depicted in FIG. 4B, where mean and 95% bound predictions are shown.

5.4 Fatigue Life Prediction Using NDE Data—No Flaw Indication

A start-up and a successive shutdown of the rotor forms a fatigue load cycle. Between the start-up and shutdown, the rotor is rotated at a constant speed. The combined loading effect from centrifugal stress, thermal stress, and residual stress is generally a constant. Because the rotation speed and temperature has minimal variations for each of such cycles, the fatigue load can safely be considered as a constant amplitude load. In this example, the average time period between a start-up and shutdown is 150 hours, and the maximum stress and the minimal stress of the fatigue load cycle are 600 MPa and 60 MPa, respectively. The critical stress intensity factor (model I fracture toughness) of Cr—Mo—V material at 800 degrees F. is $K_{Ic} = 4865$ MPa$\sqrt{\text{mm}}$ (140 KSI$\sqrt{\text{in}}$). See Hudak, S Swaminathan, V., Leverant, G., Sexena, A., Adefris, N. "Steam Turbine Rotor Life and Extension: Evaluation Of Retired Rotors", volume 2: Mechanical Properties of Service-Exposed Rotors, Tech. Rep., Electric Power Research Institute, Palo Alto, Calif., 1994. The critical crack size is obtained as $a_c = 27.7$ mm by equating the critical stress intensity factor with the stress intensity factor under the load condition. The first scheduled ultrasonic NDE testing was performed after the first 15-year service and no indication was reported from the NDE testing data. The PDF of the size of NDE-invisible flaws is expressed as $$f_{A|D}(a) = \frac{[1 - POD(a)] f_A(a)}{\int_0^\infty [1 - POD(a)] f_A(a) \, da}. \quad (24)$$

where $f_A(a)$ is the prior PDF of the flaw size and $POD(a)$ is given in Eq. (20). If no information about $f_A(a)$ is available an ignorance prior, i.e., a uniform distribution over a certain range, may be used. In this case, the $f_A(a)$ is a constant value and will be canceled out when evaluating Eq. (24). For demonstration purposes, this treatment of $f_A(a)$ is used in the application example. The fatigue life prediction is made using Eq. (21) and $4 \times 10^8$ MC simulations. Random instances of model parameters and actual flaw size are drawn according to Eq. (23) and Eq. (24), respectively. For each of the random instances, the fatigue life is obtained by cycle integration of Eq. (21) from the initial crack size to the critical crack size. The failure event at cycle number N is defined such that the crack size is larger than the critical crack size. Different settings for $\hat{a}_{th}$ and corresponding results are now described.

Case 1: Detection Threshold $\hat{a}_{th} = 0.5$ mm

Using numerical quadrature, the normalizing constant (denominator) of Eq. (24) are obtained as 0.606 for $\hat{a}_{th} = 0.5$ mm. The actual flaw size distribution is given by $$f_{A|D}(a) = 3.302 \left[ 1 - \Phi\left( \frac{\ln a + 1.6334}{0.9368} \right) \right].$$

Figure 5A:
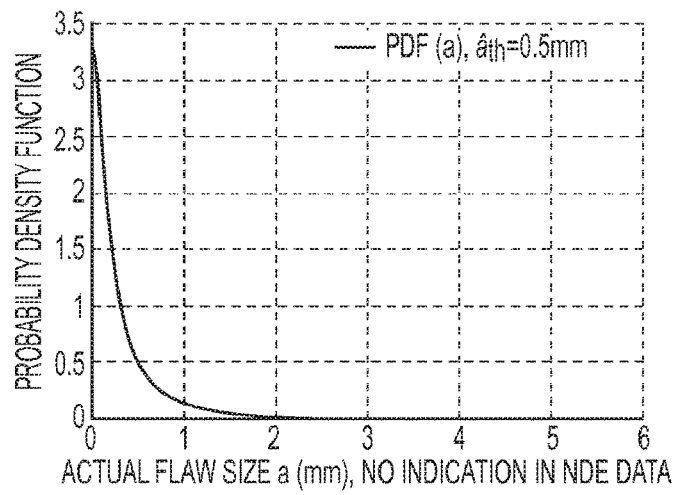
FIG. 5A, FIG. 5B, and FIG. 5C depict actual flaw size distribution, fatigue life distribution, and probability of failure ("PoF") results, respectively, for a detection threshold of 0.5 mm.
Figure 5B:
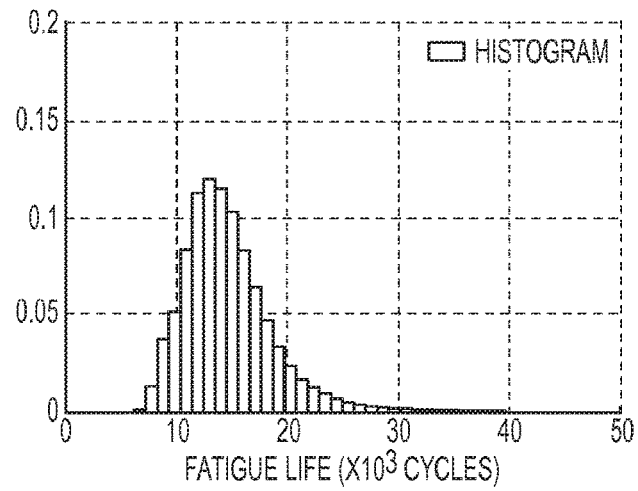
Figure 5C:
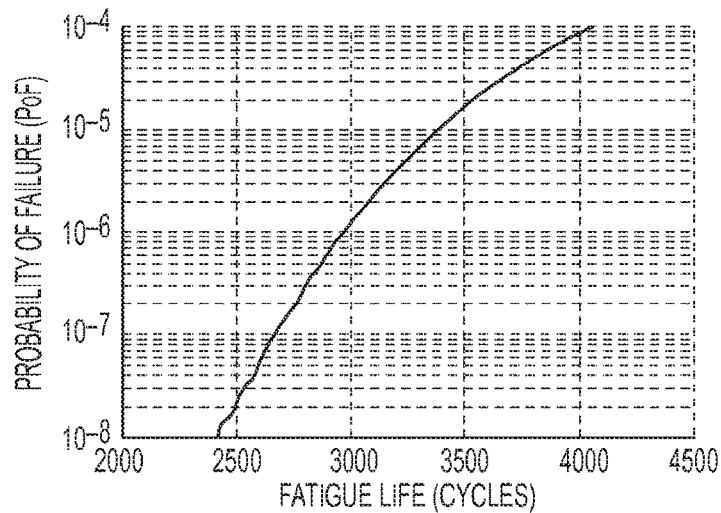

The actual flaw size distribution, fatigue life distribution, and PoF results are shown in FIG. 5A, FIG. 5B, and FIG. 5C, respectively.

Case 2: Detection Threshold $\hat{a}_{th} = 1.0$ mm

For $\hat{a}_{th} = 1.0$ mm, the normalizing constant is calculated as 0.869 and the distribution of the actual flaw size is $$f_{A|D}(a) = 1.151 \left[ 1 - \Phi\left( \frac{\ln a + 0.5793}{0.9368} \right) \right].$$

Figure 6A:
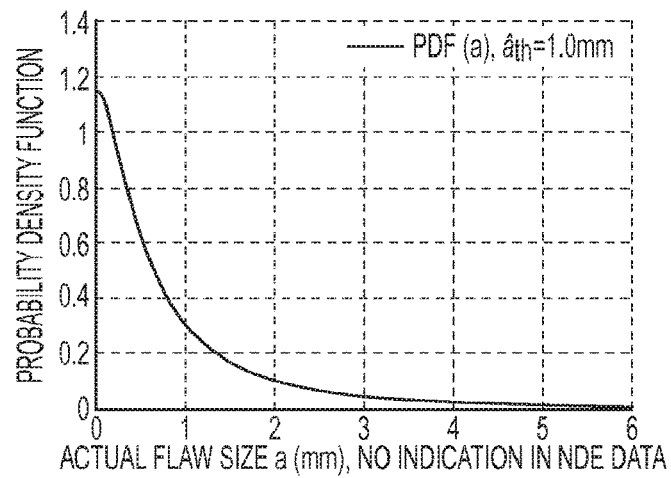
FIG. 6A, FIG. 6B, and FIG. 6C depict actual flaw size distribution, fatigue life distribution, and PoF results, respectively, for a detection threshold of 1.0 mm.
Figure 6B:
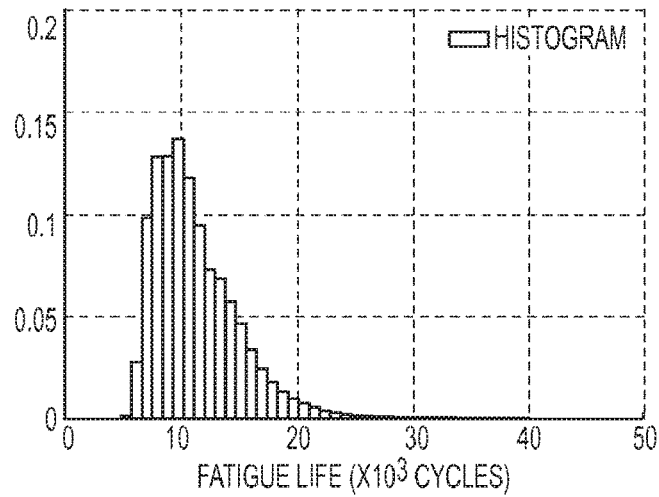
Figure 6C:
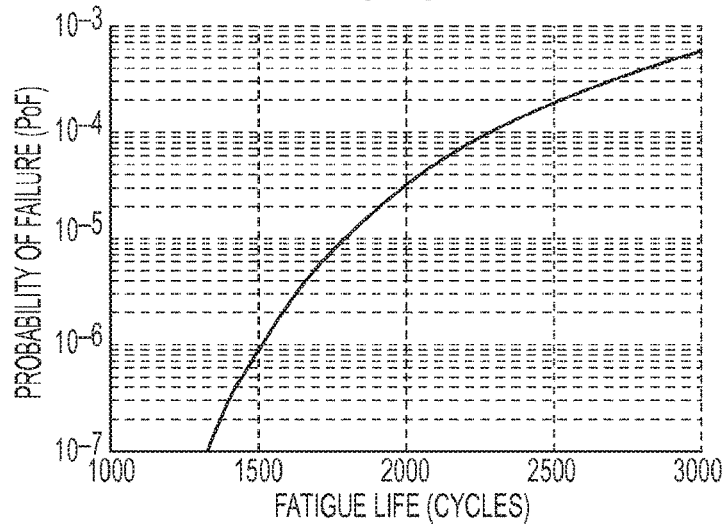

The actual flaw size distribution, fatigue life distribution, and PoF results for this case are shown in FIG. 6A, FIG. 6B, and FIG. 6C, respectively.

Case 3: Detection Threshold $\hat{a}_{th} = 1.5$ mm

For $\hat{a}_{th} = 1.5$ mm, the normalizing constant is calculated as 1.073 and the distribution of the actual flaw size is $$f_{A|D}(a) = 0.621 \left[ 1 - \Phi\left( \frac{\ln a - 0.0374}{0.9368} \right) \right].$$

Figure 7A:
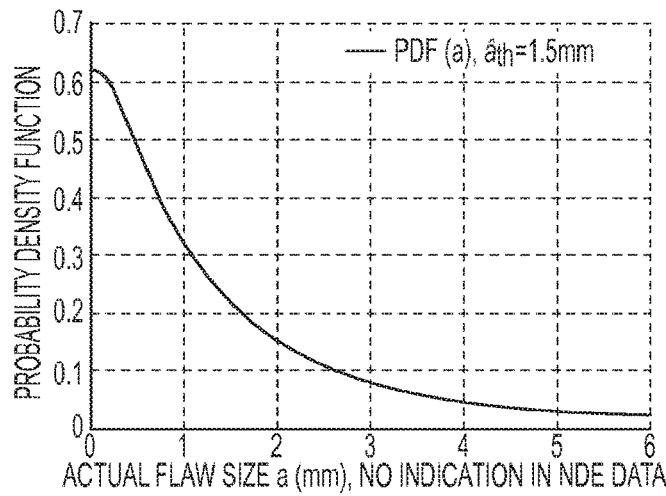
FIG. 7A, FIG. 7B, and FIG. 7C depict actual flaw size distribution, fatigue life distribution, and PoF results, respectively, for a detection threshold of 1.5 mm.
Figure 7B:
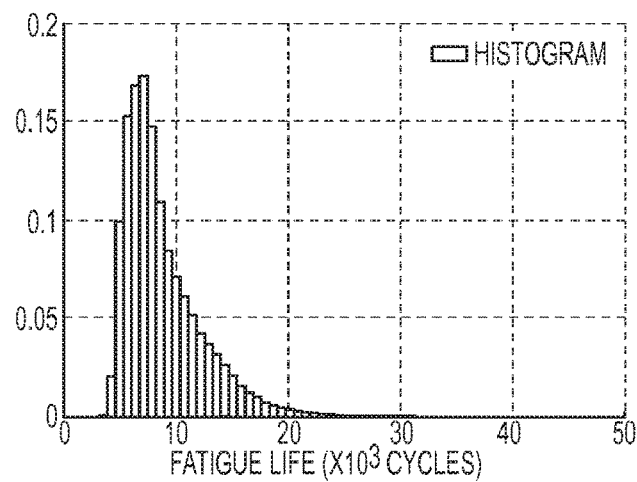
Figure 7C:
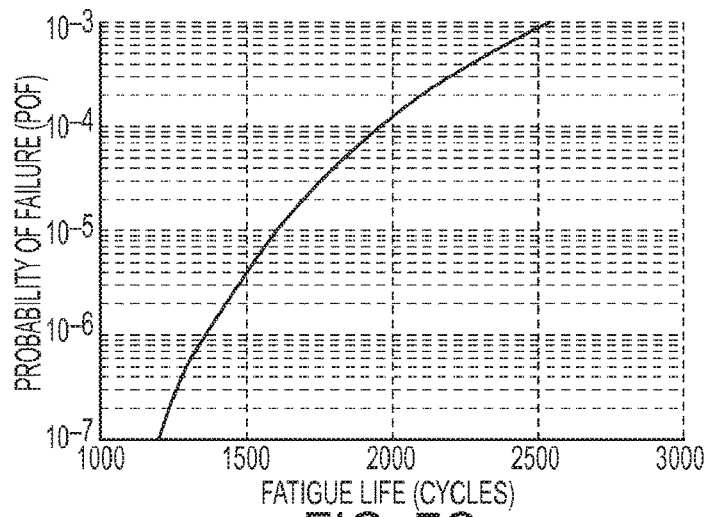

Results for the actual flaw size distribution, the fatigue life distribution, and PoF for this case are presented in FIG. 7A, FIG. 7B, and FIG. 7C, respectively.

If the maximum risk of failure for this inspected forging part is $10^{-6}$ failures/year and other forging parts are in good condition, the rotor can be used for about 2970 cycles or 50.9 ($2970 \times 150/24/365$) years equivalently given the detection threshold $\hat{a}_{th} = 0.5$ mm. For $\hat{a}_{th} = 1.0$ mm and $\hat{a}_{th} = 1.5$ mm, this number is reduced to 1510 cycles (25.8 years) and 1364 cycles (23.4 years), respectively. The first 15-year service NDE inspection results suggest that the rotor is in good service condition. The next NDE testing should be the performed after the second 15-year service.

5.5 Fatigue Life Prediction Using NDE Data—with Flaw Indications

Figure 8:
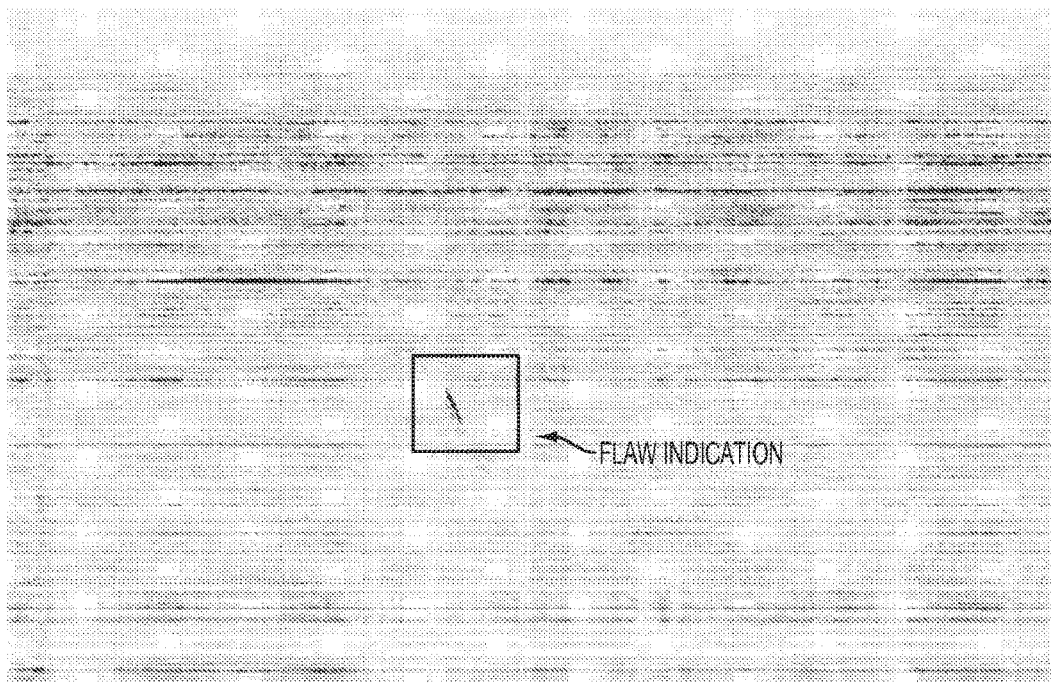
FIG. 8 depicts a flaw indication found in NDE data performed after a year service life.

A second ultrasonic NDE testing was performed after a 30-year service and one indication was found in the NDE data, as shown in FIG. 8. The reported size of the indication is a'=1.8 mm using the DGS method. The PDF of the flaw size with the indication is $$f_{A|D}(a) = \frac{1}{0.9368 a} \phi\left( \frac{\ln a - (\ln 1.8 - 0.381)/0.658}{0.9368} \right). \quad (25)$$

Figure 9A:
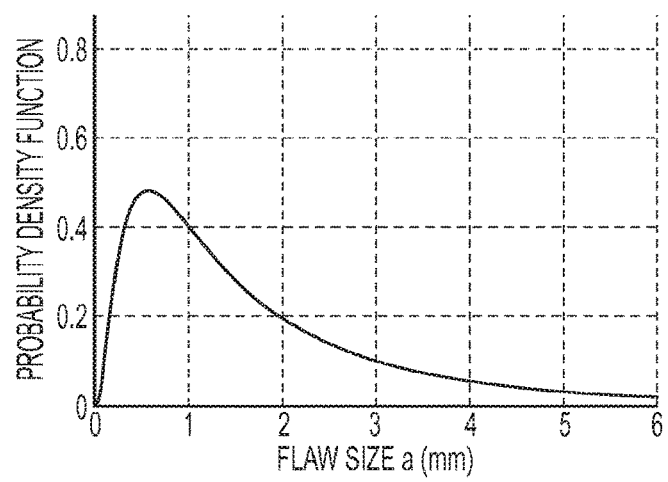
FIG. 9A, FIG. 9B and FIG. 9C depict a probability density function of a flaw size, fatigue life prediction and PoF evaluations, respectively.
Figure 9B:
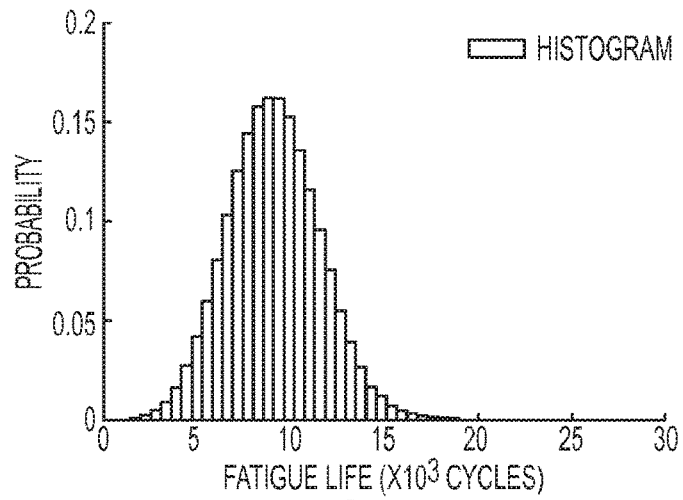
Figure 9C:
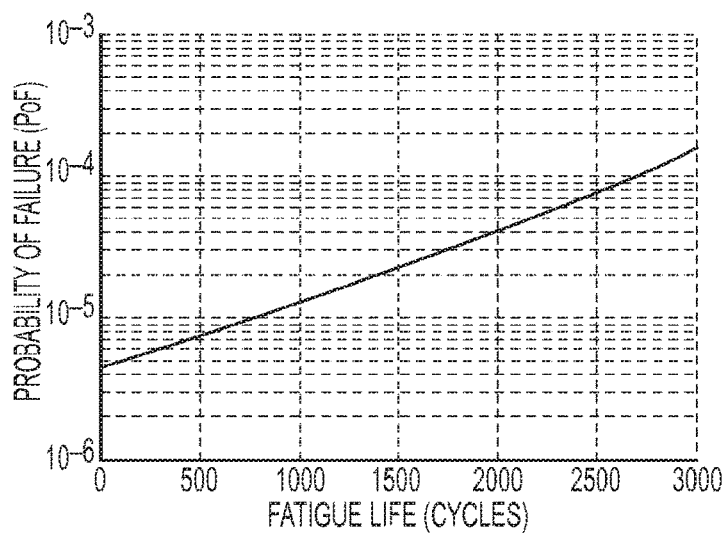

It is noted that the actual flaw distribution given a reported indication size is independent of the detection threshold $\hat{a}_{th}$. $4 \times 10^8$ MC simulations are performed. The fatigue life prediction using MC simulations follows the same procedure in Section 5.4 of the current description. The distribution of the flaw size is shown in FIG. 9A. Fatigue life predictions and PoF evaluations are presented in FIG. 9B and FIG. 9C, respectively. It is noted that even if a flaw is identified from the NDE inspection data, there can still be NDE-invisible flaws in addition to the detected ones. Fatigue life prediction of the flaws follows section 5.4 and is not repeated here. In general, the NDE-invisible flaws are relatively less risky than those identified in NDE data. In cases where flaws are identified by NDE inspection, the NDE-invisible flaw can be safely omitted for life evaluation, unless the NDE identified flaws are in uncritical regions with very low stresses acting during service.

5.6 Risk Analysis and Error Estimate

Risk analysis depends on the interpretation of the safety parameters. For example, the U.S. Nuclear Regulatory Commission (hereinafter "NRC") has approved risk levels for nuclear power plants of $10^{-4}$ failures/year for rotor disk bursts under favorable configurations, and $10^{-5}$ failures/year for rotor disk bursts under unfavorable configurations. A favorable configuration refers to the case when the pressure vessel and nuclear fuel rods are not to the side of the turbine. In addition, the risk level approved by NRC accounts for the entire rotor disk. When multiple forging parts are considered, uniformly assigning the overall risk to each of the parts should be considered. For instance, if ten forging parts are considered under the overall risk level of $10^{-4}$ failures/year, the risk assigned to each of the ten parts are $10^{-5}$ failures/year. This component risk could be used to evaluate the remaining useful life for the part containing a flaw. The uniform distribution of risk to the number of rotor components, when only evaluating the most critical ones, can be considered as conservative as the total risk for the entire rotor is approximately the sum of the individual risks (low risk approximation). A more accurate evaluation would be the calculation of the total rotor risk and its comparison to the acceptable risk limit of $10^{-4}$ per year. See, Standard Review Plan for the Review of Safety Analysis Reports for Nuclear Power Plants, Washington, D.C., US Nuclear Regulatory Commission, Office of Nuclear Reactor Regulation, LWR ed., 1987. Based on different recommended failure rates for the rotor, a more detailed table can be built for decision-making, as shown in Table 1. For example, consider the cases that only one flaw is found in the entire rotor. Using the recommended failure rate of $10^{-5}$ assigned to the forging part having a flaw of 1.8 mm, the rotor can still be safely used for about 13.2 years and another NDE testing can be scheduled after another 10-year service. However, using the recommended failure rate of $5 \times 10^{-6}$ assigned to the forging part having a flaw of 1.8 mm, the rotor can only be used for about 1.8 years. It is possible that the rotor component might need a replacement after the evaluation.

In use, the start-up and shutdown operations are not frequently performed. For example, an average duration between a start-up and a successive shutdown is approximately 100-150 hours or even longer for a modern power plant. This means that the average duration of one fatigue load cycle is approximately 100-150 hours. Although the predicted life is usually represented in terms of years, the corresponding number of cycles is only a few thousand load cycles. Error analysis of the estimation depends on basic properties of MC simulation methods.

TABLE 1

Fatigue life based on different failure rate requirements.
Duration of each cycle is considered as 150 hours.

| Component Risk (failures/year) | $2.5 \times 10^{-6}$ | $5 \times 10^{-6}$ | $7.5 \times 10^{-6}$ | $1.0 \times 10^{-5}$ |
|---|---|---|---|---|
| Life (years): No flaw, $\hat{a}_{th} = 0.5$ mm | 53.3 | 55.5 | 56.8 | 57.8 |
| Life (years): No flaw, $\hat{a}_{th} = 1.0$ mm | 27.5 | 28.9 | 29.9 | 30.7 |
| Life (years): No flaw, $\hat{a}_{th} = 1.5$ mm | 24.9 | 26.1 | 26.9 | 27.5 |
| Life (years): 1.8 mm flaw | 0 | 1.8 | 8.4 | 13.2 |

Consider the rotor failure as a rare event (i.e., PoF is approximately $10^{-8} \sim 10^{-5}$) in cases of no indication or small indications. The number of MC simulations must be carefully chosen in order to obtain a reliable estimation of PoF. The MC estimation of PoF using N random samples is $$\widetilde{PoF}_{MC} = \frac{1}{N}\sum_{i=1}^{N} 1, \tag{26}$$

where 1 is a function taking value 1 if the calculation using ith random sample produces a failure event and taking value 0 otherwise. The variance of the estimator is estimated as $$\text{Var}(\widetilde{PoF}_{MC}) = \frac{1}{N-1}\left[\frac{1}{N}\sum_{i=1}^{N} 1^2 - \widetilde{PoF}_{MC}^2\right]. \tag{27}$$

It is well known that the relative error of the MC estimator is expressed as $$RE_{MC} \stackrel{def}{=} \frac{\sqrt{\text{Var}(\widetilde{PoF}_{MC})}}{PoF} \approx \sqrt{\frac{1}{N \cdot PoF}}. \tag{28}$$

Figure 10A:
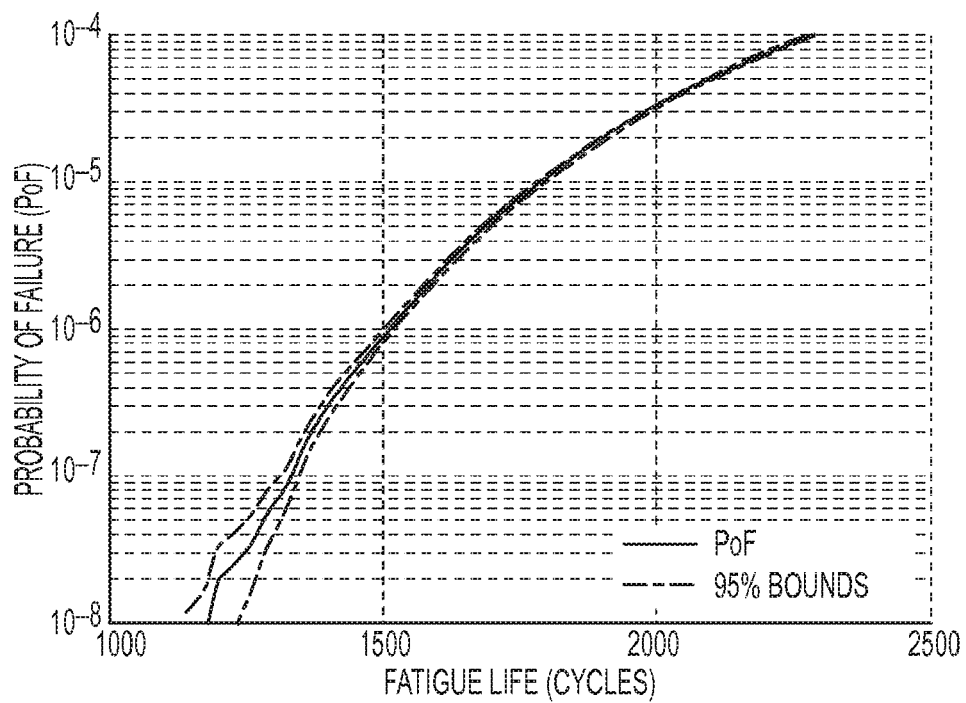
Figure 10B:
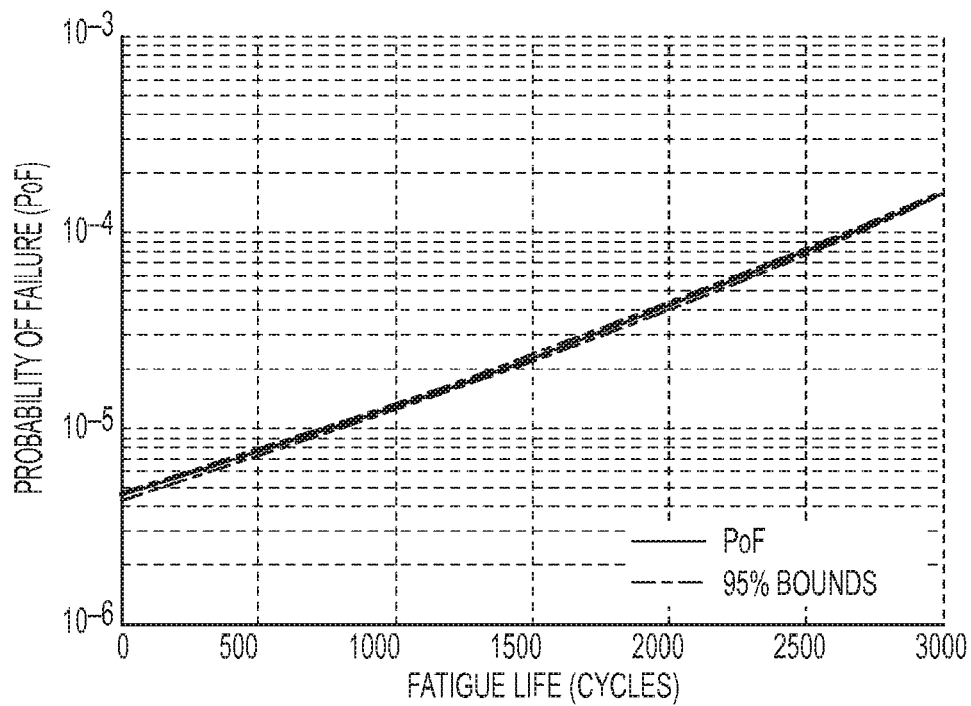

For example, to obtain a relative error of 5% for $PoF=10^{-6}$, $N=4 \times 10^{8}$ MC simulations are needed based on Eq. (28). In addition, from the known Central Limit Theorem, a confidence interval $CI=[PoF^-, PoF^+]$ can be defined for the threshold $1-2\xi$. It is such that $Pr(PoF^- < \widetilde{PoF}_{MC} < PoF^+)$, and the CI can be expressed as $$CI \approx \left[\widetilde{PoF}_{MC} - z_\xi\sqrt{\text{Var}(\widetilde{PoF}_{MC})} \ \ \widetilde{PoF}_{MC} + z_\xi\sqrt{\text{Var}(\widetilde{PoF}_{MC})}\right], \tag{29}$$

where $z_\xi = \Phi^{-1}(1-\xi)$ and $\Phi^{-1}(\cdot)$ is the inverse CDF of the standard normal variable. For instance, if the threshold is chosen as 95% then and $\xi=2.5\%$ and $z_\xi \approx 1.96$. FIGS. 10A-10B depicts median and 95% CI estimation of PoF. In particular, FIG. 10A depicts the case where no indication is found in ultrasonic NDE data and $\hat{a}_{th}=1.0$ and FIG. 10B depicts the case with a 1.8 mm indication. As such, FIGS. 10A-10B illustrate that the uncertainty in PoF prediction can be quantified using probabilistic results (i.e., 95% bounds prediction). A 95% bounds prediction provides a measure to help one to understand the extent of the scattering for the predicted POF. For example, if the bounds are relatively wide, the uncertainty of the predicted POF is large. If the bounds are narrow, the PoF prediction results are more reliable.

Three threshold values are used to demonstrate that a chosen or estimated decision limit can significantly affect the final results. In addition, a consideration is the transition of an embedded flaw to a surface flaw. If the embedded flaw is close to the surface it is possible to propagate and become a surface flaw. In this case, the flaw is no longer treated as an embedded elliptical one. The calculation should use a different geometry correction and compute the new crack size for calculation under the new geometry configuration.

6. Conclusion

The current invention provides a systematic method and procedure for probabilistic fatigue life prediction considering uncertainties from NDE inspection and fatigue model parameters. POD modeling is established using a classical log-linear model coupling the actual flaw size and the NDE reported size. The PDF of the actual crack size is derived considering three typical scenarios of NDE data: 1) no indication, 2) with flaw indications and a deterministic model converting NDE signals to flaw sizes, and 3) with flaw indications and a probabilistic conversion model. An application of steam turbine rotor integrity assessment with ultrasonic NDE inspection data is used to demonstrate the overall methodology. The current invention sets forth the formulation of a general methodology for probabilistic fatigue life prediction by developing uncertainty quantification models for NDE inspection, sizing, and model parameters. In addition, probability distributions of the actual flaw size under different NDE data scenarios are developed based on probabilistic modeling and Bayes' theorem. The derivation and results are general and can readily be adapted to different NDE applications. Further, a real world application example of a steam turbine rotor with ultrasonic NDE data is presented to demonstrate the overall methodology. The interpretation and criterion of risk parameters follow the NRC recommendations for industrial applications.

It is understood that the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 11:
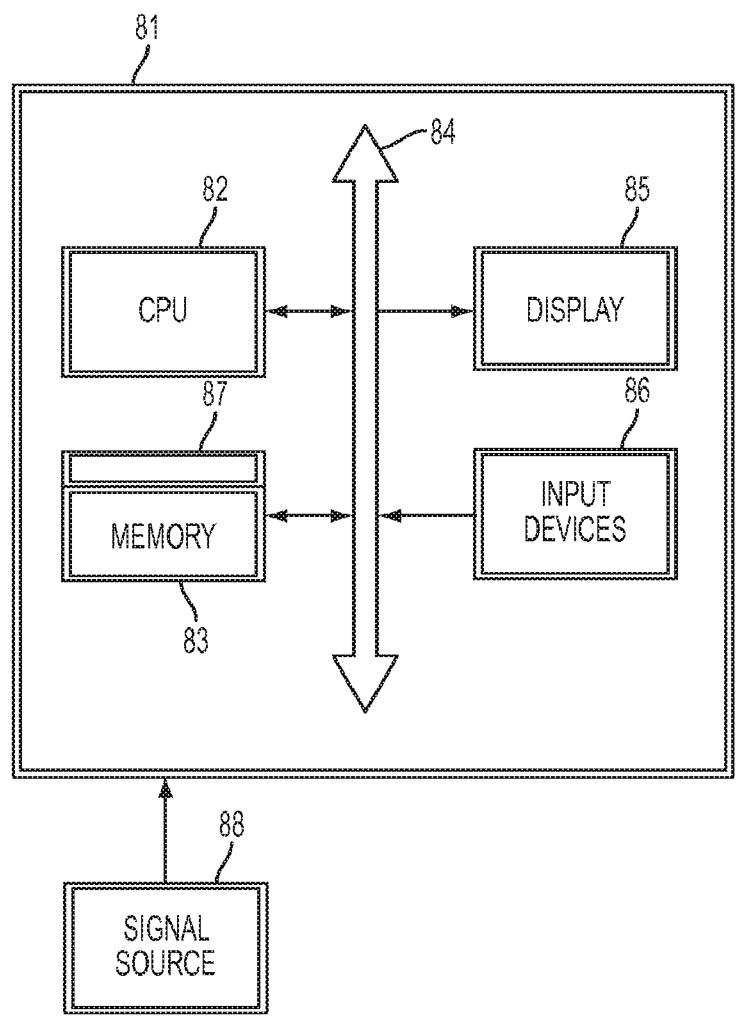
FIG. 11 is a block diagram of an exemplary computer system for implementing a method for probabilistic fatigue life prediction using ultrasonic NDE data, according to an embodiment of the invention.

FIG. 11 is a block diagram of an exemplary computer system for implementing a method for probabilistic fatigue life prediction using ultrasonic NDE data according to an embodiment of the invention. Referring now to FIG. 11, a computer system 81 for implementing the present invention can comprise, inter alia, a central processing unit (CPU) 82, a memory 83 and an input/output (I/O) interface 84. The computer system 81 is generally coupled through the I/O interface 84 to a display 85 and various input devices 86 such as a mouse and a keyboard. The support circuits can include circuits such as cache, power supplies, clock circuits, and a communication bus. The memory 83 can include random access memory (RAM), read only memory (ROM), disk drive, tape drive, etc., or a combinations thereof. The present invention can be implemented as a routine 87 that is stored in memory 83 and executed by the CPU 82 to process the signal from the signal source 88. As such, the computer system 81 is a general purpose computer system that becomes a specific purpose computer system when executing the routine 87 of the present invention.

The computer system 81 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to exemplary embodiments, those skilled in the art will appreciate that various modifications and substitutions can be made thereto without departing from the spirit and scope of the invention as set forth in the appended claims.

What is claimed is:

1. A method for probabilistic fatigue life prediction of a turbine part, comprising:
in a fatigue life prediction processor, receiving a probability of detection model;
in the fatigue life prediction processor, receiving an initial crack size probability density function (PDF) for the turbine part based on the received probability of detection model;
in the fatigue life prediction processor, receiving probabilistic identification of model parameters;
in the fatigue life prediction processor, receiving a model parameter PDF based on the received probabilistic identification of model parameters according to:

$$f(\ln C, m) \sim \text{MVN}(\mu_{(\ln C, m)}, \Sigma_{(\ln C, m)}),$$

where MVN is a multivariate normal distribution, C and m are model parameters from fatigue testing data, $\mu_{(\ln C,m)}$ is a mean vector and $\Sigma_{(\ln C,m)}$ is a covariance matrix;
receiving a crack growth model based on the received initial crack size PDF, the model parameter PDF and material/load factors;
determining uncertainty propagation using an analytical or simulation-based method based on the crack growth model based on uncertainty of at least one of material properties, geometries, sensitivity of instruments, and loading of the turbine part;
in the fatigue life prediction processor, computing a fatigue life prediction for the turbine part based on the uncertainty propagation and crack growth model; and
implementing a maintenance plan for the turbine part based on the fatigue life prediction.

2. The method according to claim 1, wherein nondestructive examination (NDE) data and NDE sizing data is used in the probability of detection model.

3. The method according to claim 1, wherein the fatigue testing data is used for providing probabilistic identification of model parameters.

4. The method according to claim 1, wherein the probability of detection model is:

$$POD(a) = Pr(\alpha + \beta \ln a + \varepsilon > \ln \hat{a}_{th}) = \Phi\left(\frac{\ln a - (\ln \hat{a}_{th} - \alpha)/\beta}{\sigma_\varepsilon/\beta}\right)$$

where a is an actual size of a flaw, $\alpha$ and $\beta$ are fitting parameters, $\varepsilon$ is a normal random variable with zero mean and standard deviation $\sigma_\varepsilon$, $\hat{a}_{th}$ is a predefined threshold and $\Phi(\cdot)$ is a standard normal cumulative distribution function.

5. The method according to claim 4, wherein parameters $\alpha$, $\beta$ and $\varepsilon$ are estimated using:

$$\ln \hat{a} = \alpha + \beta \ln a + \varepsilon$$

where â is a reported flaw size based on an ultrasonic NDE signal, a is the actual size of a flaw, $\alpha$ and $\beta$ are fitting parameters, ε is a normal random variable with zero mean and standard deviation $\sigma_\epsilon$.

6. The method according to claim 1, wherein the initial crack size PDF is determined by:

$$p(A|D) = f_{A|D}(a) = \frac{1}{a(\sigma_\varepsilon/\beta)} \phi\left(\frac{\ln a - (\ln a' - \alpha)/\beta}{\sigma_\varepsilon/\beta}\right)$$

where a is an actual size of a flaw, α and β are fitting parameters, $\sigma_\epsilon$ is a standard deviation, a' is a value of a reported flaw size and $\Phi(\cdot)$ is a standard normal probability density function.

7. The method according to claim 1, wherein the initial crack size PDF is determined by:

$$p(A|D) = f_{A|D}(a) = \frac{1}{a\left(\sqrt{\sigma_e^2+\sigma_\varepsilon^2}/\beta\right)} \phi\left(\frac{\ln a - (\ln a' - \alpha)/\beta}{\sqrt{\sigma_e^2+\sigma_\varepsilon^2}/\beta}\right)$$

where a is an actual size of a flaw, α and β are fitting parameters, $\sigma_\epsilon$ is a standard deviation, $\sigma_e$ is a standard deviation of a random quantity e representing the difference between a probabilistic flaw size model output and an estimated crack size, a' is the value of the reported flaw size and $\Phi(\cdot)$ is a standard normal probability density function.

8. The method according to claim 1, wherein the initial crack size PDF is determined by:

$$p(A|\overline{D}) = f_{A|\overline{D}}(a) = \frac{\partial[Pr(A \le a|\overline{D})]}{\partial a} = \frac{[1-POD(a)]f_A(a)}{\int_0^\infty [1-POD(a)]f_A(a)da}$$

where a is an actual size of a flaw, A is a log-normal variable and $\overline{D}$ is the event that a flaw is not identified.

9. The method according to claim 1, wherein the material/load factors include a stress intensity factor given by:

$$K=\sigma\sqrt{\pi a} M/Q[\sin^2 \lambda+(a/c)^2 \cos^2 \lambda]^{1/4}$$

where K is a stress intensity factor of a point located at an angle λ with respect to the direction of the applied tensile stress σ, M is a location factor, a is an initial crack size of an embedded elliptical crack which is also a minor axis length of a semi-ellipse, c is a major axis length of the semi-ellipse and Q is a shape factor.

10. The method according to claim 1, wherein the crack growth model is given by:

$$da/dN=C(\Delta K)^m$$

where a is a crack size, N is the number of load cycles, C and m are model parameters identified from fatigue testing data and ΔK is a stress intensity factor range for one load cycle.

11. A non-transitory program storage device readable by a computer, tangibly embodying a program of instructions executed by a fatigue life prediction processor to perform methods steps for probabilistic fatigue life prediction for a part of a turbine, the method comprising the steps of:

in the fatigue life prediction processor, receiving a probability of detection model;

in a fatigue life prediction processor, receiving an initial crack size probability density function (PDF) for the turbine part based on the received probability of detection model;

in the fatigue life prediction processor, receiving probabilistic identification of model parameters;

in the fatigue life prediction processor, receiving a model parameter PDF based on the received probabilistic identification of model parameters according to:

$$f(\ln C, m) \sim MVN(\mu_{(\ln C, m)}, \Sigma_{(\ln C, m)}),$$

where MVN is a multivariate normal distribution, C and m are model parameters from fatigue testing data, $\mu_{(\ln C,m)}$ is a mean vector and $\Sigma_{(\ln C,m)}$ is a covariance matrix;

providing a crack growth model based on the received initial crack size PDF, the model parameter PDF and material/load factors;

determining uncertainty propagation using an analytical or simulation-based method based on the crack growth model based on uncertainty of at least one of material properties, geometries, sensitivity of instruments, and loading of the turbine part;

providing fatigue life prediction based on the uncertainty propagation and crack growth model; and implementing a maintenance plan for the turbine part based on the fatigue life prediction.

12. The computer readable program storage device according to claim 11, wherein nondestructive examination (NDE) data and NDE sizing data is used in the probability of detection model.

13. The computer readable program storage device according to claim 11, wherein the fatigue testing data is used for providing probabilistic identification of model parameters.

14. The computer readable program storage device according to claim 11, wherein the probability of detection model is:

$$POD(a) = Pr(\alpha + \beta \ln a + \varepsilon > \ln \hat{a}_{th}) = \Phi\left(\frac{\ln a - (\ln \hat{a}_{th} - \alpha)/\beta}{\sigma_\varepsilon/\beta}\right)$$

where a is an actual size of a flaw, α and β are fitting parameters, ε is a normal random variable with zero mean and standard deviation $\sigma_\epsilon$, $\hat{a}_{th}$ is a predefined threshold and $\Phi(\cdot)$ is a standard normal cumulative distribution function.

15. The computer readable program storage device according to claim 14, wherein parameters α, β and ε are estimated using:

$$\ln \hat{a} = \alpha + \beta \ln a + \varepsilon$$

where $\hat{a}$ is a reported flaw size based on an ultrasonic NDE signal, a is the actual size of a flaw, α and β are fitting parameters, ε is a normal random variable with zero mean and standard deviation $\sigma_e$.

16. The computer readable program storage device according to claim 11, wherein the initial crack size PDF is determined by:

$$p(A|D) = f_{A|D}(a) = \frac{1}{a(\sigma_\varepsilon/\beta)} \phi\left(\frac{\ln a - (\ln a' - \alpha)/\beta}{\sigma_\varepsilon/\beta}\right)$$

where a is an actual size of a flaw, α and β are fitting parameters, $\sigma_\epsilon$ is a standard deviation, a' is a value of a reported flaw size and $\Phi(\cdot)$ is a standard normal probability density function.

17. The computer readable program storage device according to claim 11, wherein the initial crack size PDF is determined by:

$$p(A\mid D) = f_{A\mid D}(a) = \frac{1}{a\left(\sqrt{\sigma_e^2 + \sigma_\varepsilon^2}\Big/\beta\right)} \phi\left(\frac{\ln a - (\ln a' - \alpha)/\beta}{\sqrt{\sigma_e^2 + \sigma_\varepsilon^2}\Big/\beta}\right)$$

where a is an actual size of a flaw, α and β are fitting parameters, $\sigma_\epsilon$ is a standard deviation, $\sigma_e$ is a standard deviation of a random quantity e representing the difference between a probabilistic flaw size model output and an estimated crack size, a' is the value of the reported flaw size and $\Phi(\cdot)$ is a standard normal probability density function.

* * * * *